(12) United States Patent
Feldcamp

(10) Patent No.: US 7,938,641 B2
(45) Date of Patent: May 10, 2011

(54) EXTRUSION DIE

(75) Inventor: Edward George Feldcamp, Gloucestershire (GB)

(73) Assignee: Preform Dies Limited (GB)

( * ) Notice: Subject to any disclaimer, the term of this patent is extended or adjusted under 35 U.S.C. 154(b) by 1091 days.

(21) Appl. No.: 10/240,476

(22) PCT Filed: Mar. 27, 2001

(86) PCT No.: PCT/GB01/01325
§ 371 (c)(1), (2), (4) Date: Jan. 21, 2003

(87) PCT Pub. No.: WO01/74506
PCT Pub. Date: Oct. 11, 2001

(65) Prior Publication Data
US 2005/0029705 A1 Feb. 10, 2005

(30) Foreign Application Priority Data
Apr. 1, 2000 (GB) .................................. 0007948.3

(51) Int. Cl.
*B29C 47/20* (2006.01)

(52) U.S. Cl. ........ 425/380; 425/381; 425/461; 425/466; 425/467

(58) Field of Classification Search ................. 425/380, 425/381, 461, 466, 467
See application file for complete search history.

(56) References Cited

U.S. PATENT DOCUMENTS

| | | | |
|---|---|---|---|
| 5,756,016 A * | 5/1998 | Huang et al. ................. 425/461 |
| 6,062,059 A * | 5/2000 | Feldcamp ..................... 72/271 |

FOREIGN PATENT DOCUMENTS

WO  WO 99/65622  * 12/1999

* cited by examiner

*Primary Examiner* — Yogendra N Gupta
*Assistant Examiner* — Joseph Leyson
(74) *Attorney, Agent, or Firm* — Skinner and Associates

(57) ABSTRACT

An extrusion die comprises a die body defining a die cavity (18). The cavity (18) is shaped such that the die body includes a male portion (24) and a female portion (26). A leading edge (18a) of a part of one side of the die cavity (18) is out of alignment with a leading edge (18a) of an opposing part of the die cavity (18), at rest, such that, in use, when deflection of parts of the die occurs, the leading edges (18a) substantially align.

10 Claims, 5 Drawing Sheets

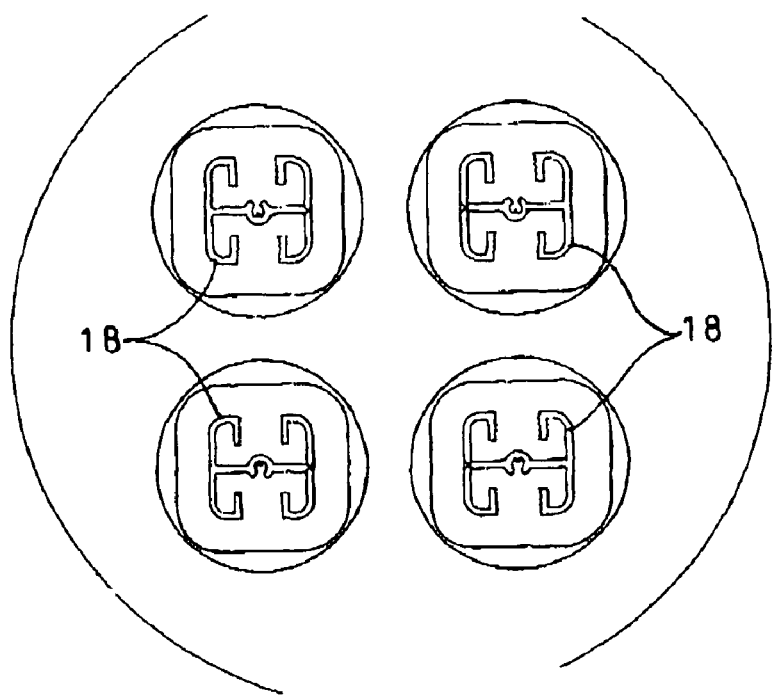
FIG 6
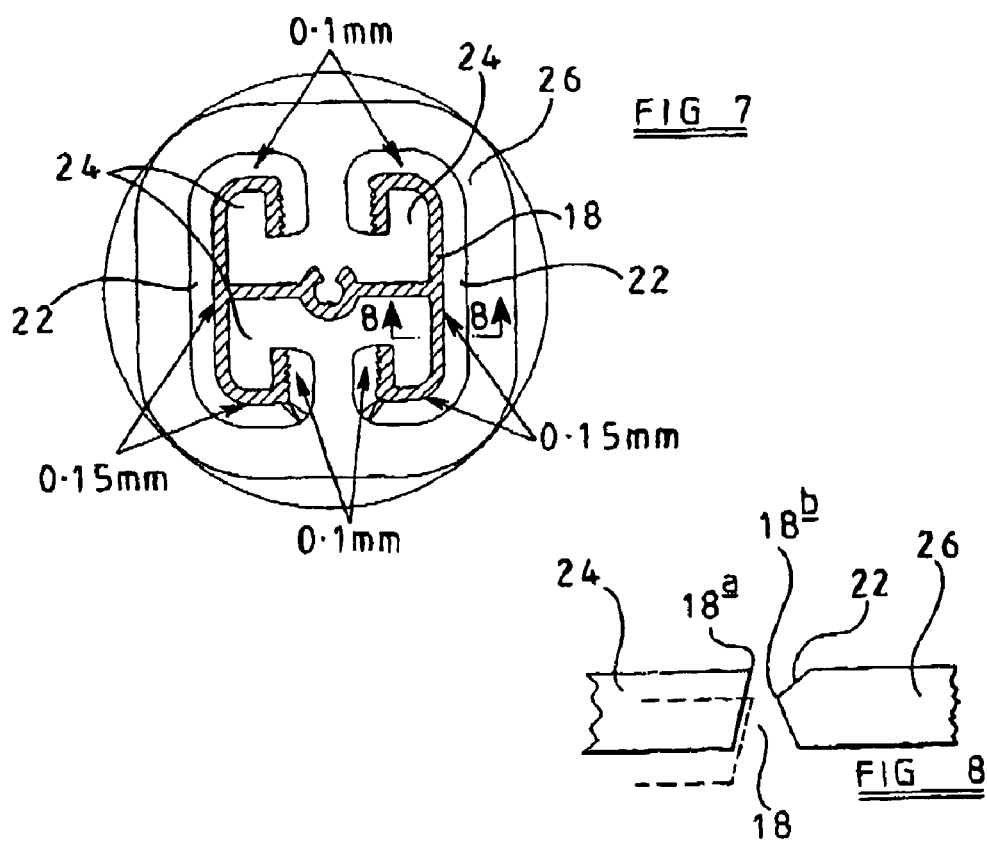
FIG 7
FIG 8

EXTRUSION DIE

FIELD

This invention relates to an extrusion die for use in the extrusion of metallic materials, and in particular to a die suitable for use in the extrusion of aluminium. The invention also relates to a method of manufacturing a die of this type.

BACKGROUND INFORMATION

When extruding aluminium it is important to ensure that the speed of movement of the aluminium through the extrusion die is uniform across the die. This has been achieved in the past using a die having a die cavity of finite bearing length, and by varying the bearing length across the die. It has been found, however, that the extruded product sometimes contains surface imperfections resulting from the engagement between the bearing surface and the aluminium being extruded. Rather than provide the bearing surface downstream of the entrance to the die cavity, it is known to use a die having a so-called zero bearing, and to provide a chamber upstream of the die cavity of varying bearing length to control the extrusion speed over the die. Although the term zero bearing suggests that the die cavity is of zero bearing length, in practise the die cavity is likely to have a finite, but very small bearing length.

Another problem which has been faced when extruding aluminium is that, where the extrusion is, for example, of channel section, the sides of the channel tend to deflect thus, if the die is shaped to include a die cavity in which the parts thereof which form the sides of the channel are parallel to one another, the sides of a member extruded using the die may be splayed, rather than parallel to one another. In order to correct such splaying, it is known to provide a pre-chamber located upstream of the die cavity, the pre-chamber being of greater width than the part of the die cavity immediately adjacent therein the pre-chamber being offset laterally relative to the die cavity. Such a technique results in a side loading being applied to the metal being extruded. Although off-setting the pre-chamber laterally from the die cavity can correct splaying in some circumstances, it is of limited application and may not be able to apply a sufficient force to correct splaying in, for example, extrusions of relatively low wall thickness. Similar problems are experienced when hollow members are extruded using a die comprising a male part and a female part.

BRIEF SUMMARY

According to the present invention there is provided an extrusion die comprising a die body having a die cavity formed therein, the die body defining a male portion which projects into a female portion, and wherein the leading edge of the part of the die cavity defined by the male portion and the leading edge of the part of the die cavity defined by the female portion are not co-planar, when the die is not in use.

It has been found that, in prior arrangements, the magnitude of the load applied to the metal being extruded, and hence to the die, is sufficient to cause the male portion to deflect relative to the female portion. If the die is a zero bearing die, such deflection results in the leading edges of the die cavity being spaced apart in the extrusion direction. Such spacing results in side loadings being experienced by the metal being extruded and can result in splaying as described hereinbefore. By designing the die such that, at rest, the leading edges are not co-planar, this effect can be reduced as the die can be arranged such that the leading edges become coplanar or substantially co-planar when deflection occurs in use. Although it is convenient for the leading edges to become co-planar, the advantages of the invention also arise if, throughout the die, the leading edge of a part one side of the cavity aligns with the part thereof on the other side of the cavity.

It should be noted that, in general both of the male and the female portions deflect, and that it is the relative deflection between these portions for which the invention is intended to compensate.

Although the description herein refers to deflection, it will be appreciated that some compression of the material of the die may also occur as a result of the application of loads thereto, in use, and that the invention can also be used to overcome disadvantages associated with misalignment of bearings caused, in use, by such compression.

The die cavity is preferably shaped such at its width increases from a minimum adjacent the leading edges thereof. Such an arrangement is referred to hereinafter as a zero bearing die.

The invention is particularly advantageous with zero bearing dies as a relatively small amount of deflection causes total misalignment of the bearings of such dies. In dies of the non-zero type, even when deflection has occurred, it is likely that a part of each bearing surface will remain aligned with a part of the opposing bearing surface.

The die cavity may be shaped to define the male and female portions, the male portion taking the form of a tongue portion. In such an arrangement, the die is used to form an extruded member including at least one elongate channel of any cross-sectional shape.

The die cavity may be shaped to define at least one further tongue portion. The die body may define at least one further die cavity.

The die body may have a substantially planar front face, a groove being provided in the front face, the leading edges of the die cavity being defined at the intersection between the die cavity and the groove, the groove being of non-uniform depth.

Alternatively, the die body may have a non-planar front face, the front face having been machined to define the leading edges of the die cavity.

A preform chamber may be located upstream of the die cavity, the preform chamber being shaped to achieve a uniform extrusion speed across the die. The preform chamber may be of uniform depth, and hence of non-uniform bearing length, and/or may be of non-uniform width.

In an alternative arrangement the die may be designed to produce an extruded member of hollow form, the male portion projecting into an opening formed in the female portion.

According to another aspect of the invention there is provided a method of manufacturing an extrusion die comprising calculating the likely deflection of a male portion of the die, in use, and forming a recess around at least part of a die cavity of the die, the depth of the recess being non-uniform and shaped such that, in use, the leading edge of a part of the die cavity to one side of the cavity aligns with the leading edge on the opposing side of the cavity.

The recess is conveniently formed using a grinding operation, but it will be appreciated that other techniques could be used.

The step of calculating the likely deflection is conveniently achieved using a finite element analysis technique.

BRIEF DESCRIPTION OF THE SEVERAL VIEWS OF THE DRAWING

The invention will further be described, by way of example, with reference to the accompanying drawings, in which:

FIG. 6 is a view similar to FIG. 2 illustrating an alternative die;

FIG. 7 is a diagrammatic view illustrating one of the die cavities of the die of FIG. 6;

FIG. 8 is a diagrammatic sectional view along the Line 8-8 of FIG. 7;

DETAILED DESCRIPTION

Figure 1:
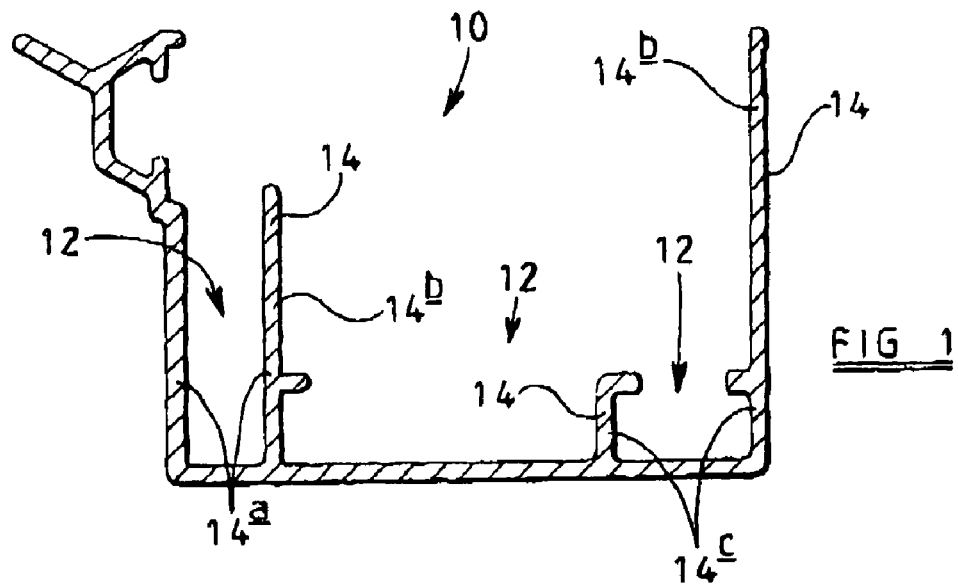
FIG. 1 is a sectional view of an extruded aluminium member.

Referring to FIGS. 1 to 4, FIG. 1 illustrates an extruded aluminium member of relatively complex shape. The member 10 includes several regions which can be regarded as channel-shaped regions 12 including limbs 14 which are generally parallel to one another. The pairs of limbs 14 forming several of the channel-shaped regions 12 illustrated in FIG. 1 are denoted by the references 14a, 14b and 14c in the drawing.

Figure 2:
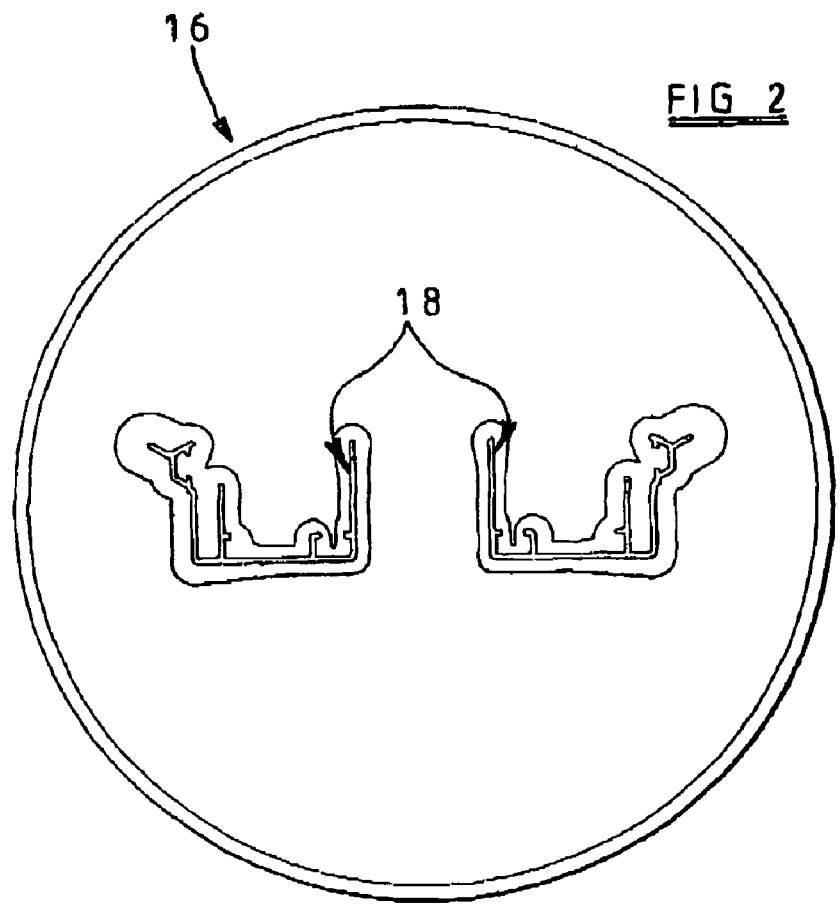
FIG. 2 is part of a view of a die used in the extrusion of the member of FIG. 1.
Figure 3:
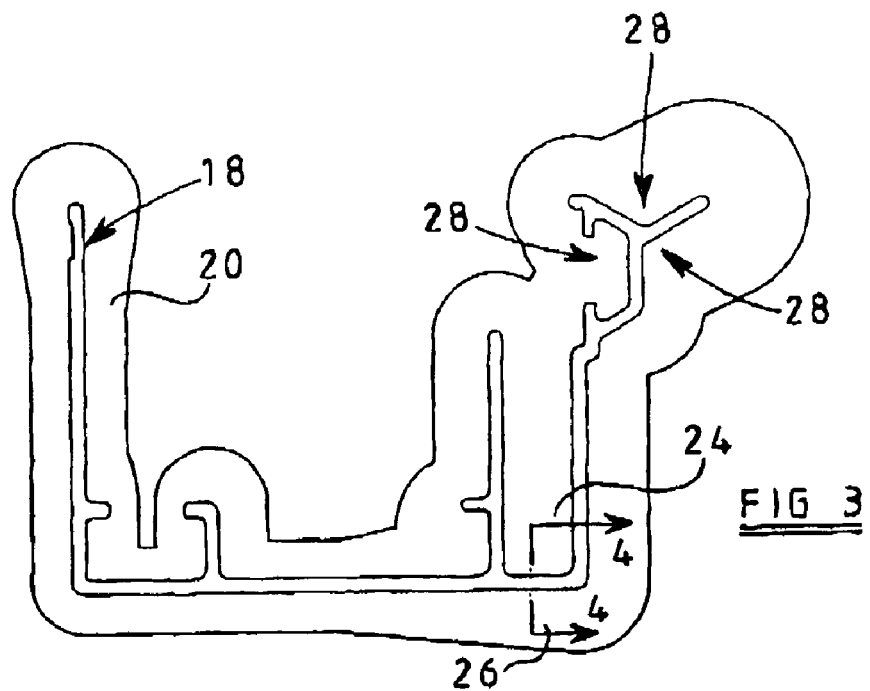
FIG. 3 is an enlargement of part of FIG. 2.

FIG. 2 illustrates part of the die body 16 of an extrusion die for use in the production of the member 10. The die body 16 is provided with openings defining a pair of die cavities 18, each die cavity 18 being designed for use in the production of the member 10. FIG. 3 illustrates one of the die cavities 18 in greater detail.

As illustrated in FIG. 3, each die cavity 18 comprises an opening shaped to conform, generally, with the cross-sectional shape of the member 10 to be extruded. The width of the cavity 18 increases from a minimum adjacent the leading edges 18a, 18b of the cavity 18 (see FIG. 4), thus the die is of the zero bearing type.

Figure 4:
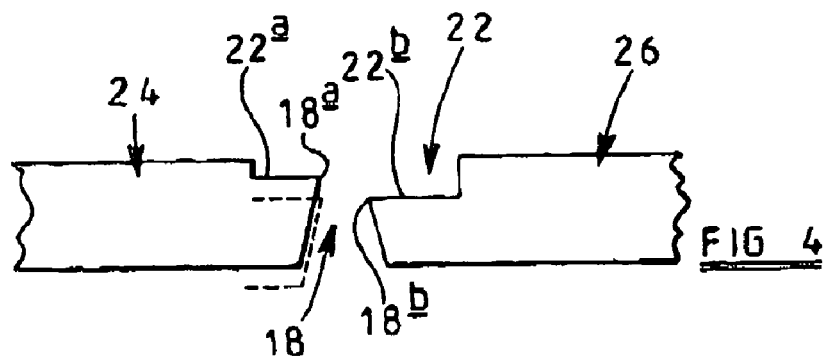
FIG. 4 is a diagrammatic sectional view along the line 4-4 of FIG. 3.

The leading surface of the die body 16 is of generally planar form, and is provided with a recess 20 aligned with and of the same general shape as the cavity 18, but of greater width. An additional recess 22 (see FIG. 4) is formed in the base of the recess 20, the recess 22 again being of the same general shape as the die cavity 18 but of greater width. As illustrated in FIG. 4, the leading edges 18a, 18b of the die cavity 18 are defined at the intersection between the die cavity 18 and the recess 22.

As best shown in FIG. 3, the part of the die body 16 located between the parts of the die cavity 18 which, in use, form each pair of limbs 14 takes the form of a tongue portion 24 received within a correspondingly shaped female portion 26 of the die body 16. In use, the application of a load to the material to be extruded tends to cause the tongue portions 24 to deflect relative to the male portions 26. In order to reduce the risk of such deflection causing the limbs 14 of the member 10 becoming splayed, or to reduce the degree by which they become splayed, the die is manufactured in such a manner that, when the die is not in use, the leading edges 18a of the die cavity 18 defined by parts of the tongue portions 24 are not co-planar with those defined by parts of the female portions 26 but rather are positioned such that the deflection of the tongue portions 24 (to the position shown in broken lines in FIG. 4) brings the leading edges 18a associated therewith closer to the plane containing the leading edges 18b associated with the female portions 26, and preferably into the same plane. By ensuring that leading edges 18a, 18b are substantial co-planar, in use the application of side loadings on the material being extruded, and hence splaying of the limbs 14 can be reduced.

In the embodiment of FIGS. 1 to 4, the recess 22 is not of uniform depth but as illustrated in FIG. 4, contains regions 22a on one side of the die cavity 18 of relatively small depth and regions 22b on the other side of the die cavity 18 of greater depth. The regions 22a are provided on the tongue portions 24, and the depths of the regions 22a, 22b are chosen to ensure that when the tongue portions 24 occupy their deflected positions, in use, the leading edges 18a, 18b are substantially co-planar.

If desired, the recess 22 may be off-set laterally from the opening of the die cavity 18 in some parts of the die, such lateral off-setting also resulting in side loadings being applied to the metal being extruded to correct for splaying of the limbs 14 in the conventional manner. This technique may be used, for example, where the amount of splaying of the limbs 14 is relatively small and may be corrected relatively easily using this technique or where the use of providing parts of the recess 22 of different depth is not practical or it is not practical to fully correct splaying using this technique.

Although as described hereinbefore, in use, the leading edges of the die cavity become co-planar or substantially coplanar, this need not be the case. In order to achieve the benefit of the invention, all that is required is that, in use, the leading edges on opposing sides of the die cavity align or substantially align with one another. The plane in which the leading edges of one part of the die align need not be the same as that in which the leading edges of other parts of the die cavity align.

Figure 5:
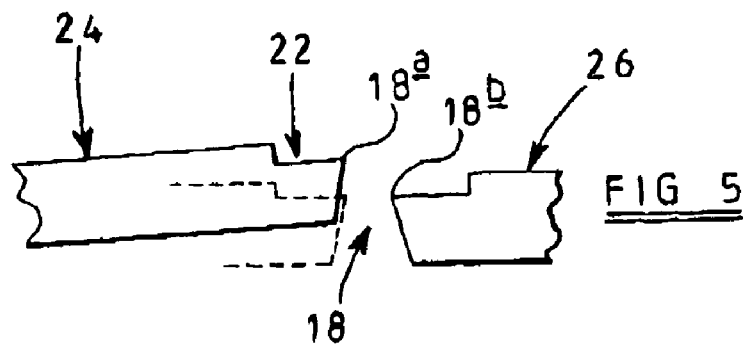
FIG. 5 is a view similar to FIG. 4 illustrating an alternative embodiment.

FIG. 5 illustrates an alternative to the arrangement of FIGS. 1 to 4. In the arrangement of FIG. 5, instead of using the recess 22 to cause the leading edges 18a, 18b to be non-co-planar, the leading face of the die body 16 is not of planar form but rather is shaped so that, for example, the leading face of the parts of the die body 16 defining the tongue portions 24 are raised relative to the parts defining the female portions 26.

It will be appreciated that in both of the arrangements described hereinbefore, the spacing of the leading edges 18a, 18b in the direction of extrusion, varies smoothly and continuously over the face of the die, for example from a maximum at the tips of the tongue portions 24 to a minimum at the ends remote therefrom.

Although in the arrangements described hereinbefore the recess 22 is of flat bottomed form, it could, if desired, be of angled form. A flow control pre-chamber of varying bearing length or shape may be provided upstream of the die cavity, if desired, to ensure that the extrusion speed across the die is substantially uniform. Alternatively, a bearing surface of variable bearing length may be provided downstream of the leading edges 18a, 18b of the die cavity to achieve this effect. Further, although in the description hereinbefore the tongue portions 24 are of parallel sided form, it will be appreciated that this need not be the case and that the invention is applicable to dies having tongue portions of any shape, for example of curved form or of V-shaped section. Several V-shaped tongue portions are illustrated in FIG. 3 and denoted by reference numeral 28.

The distances through which the tongue portions deflect, and hence the distances through which the leading edges of the die cavity should be spaced when at rest are very small.

FIG. 6 illustrates a die having four die cavities 18 formed therein, each including several tongue portions 24 and corresponding female portions 26. FIG. 7 is a view, to an enlarged scale, of one of the cavities 18 shown in FIG. 6. In FIG. 7, the shaded area is the die cavity 18. A recess 22 is formed around part of the die cavity 18 with the result that the leading edges 18a of the parts of the cavity defined by the tongue portions 24 lie in one plane and the leading edges 18b defined by the female portions 26 lie out of that plane. The recess 22 is only formed on the female portions 26 and is not of uniform depth. The depth of the recess 22 in various places is marked on the drawing. Further, the recess 22 is not of flat bottomed form, but rather is of angled form as illustrated in FIG. 8.

Figure 9:
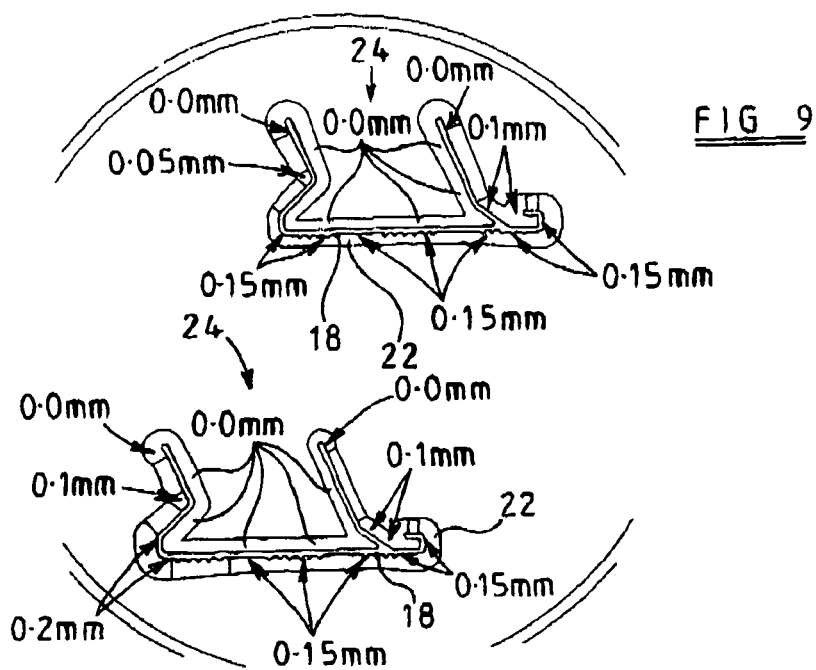
FIG. 9 is a view similar to FIG. 6 illustrating a further alternative die.

FIG. 9 illustrates a die for producing a member of an alternative cross-section, the die including two die cavities. The load experienced by the die body is not uniform but rather varies depending upon the distance from the edge of the die body. As a result, a tongue portion located near the centre of the die will deflect by a different amount from a similar tongue portion located near the edge of the die body. The spacing of the leading edges of the die cavities, at rest should be modified accordingly, and FIG. 9 indicates the spacing of the leading edges 18a, 18b at various points around the two die cavities 18, at rest.

Comparing FIG. 9 with FIG. 2, it will be appreciated that in FIG. 9 the two cavities are identical to one another, those of FIG. 2 being mirror-images of one another. It is advantageous to produce identical extrusions as any treatment processes carried out immediately after extrusion can be simplified. The technique of the present invention allows dies containing several cavities arranged to produce identical extrusions to be manufactured relatively easily. In FIG. 9, the chambers 22 are dimensioned to ensure that the correct proportions of metal to be extruded are supplied to the two die cavities 18.

Figure 10:
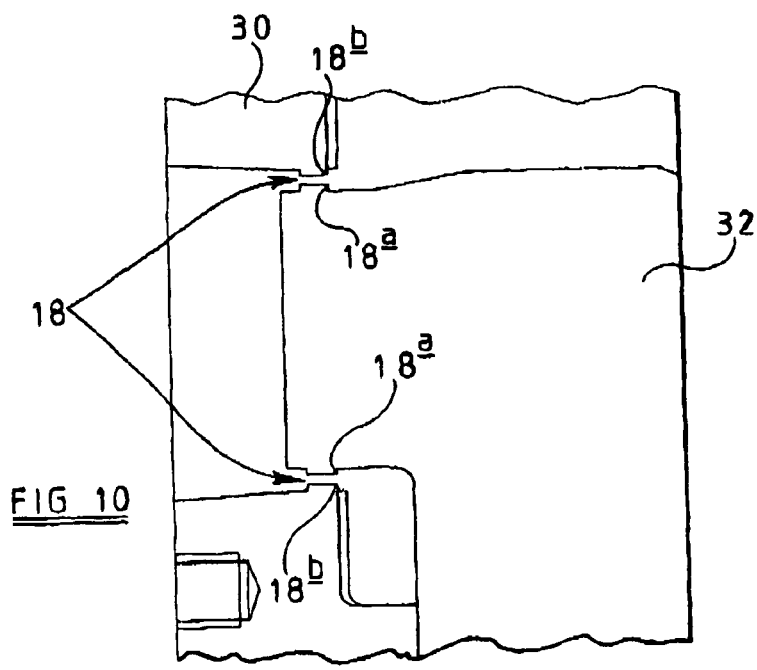
FIG. 10 is a diagrammatic sectional view illustrating an alternative die.
Figure 11:
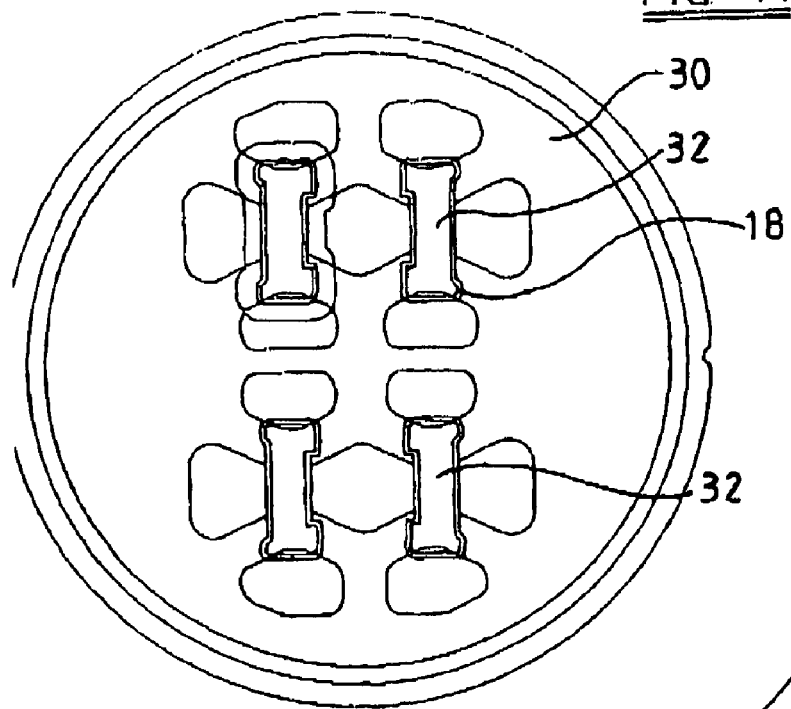
FIG. 11 is a plan view illustrating the die of FIG. 10.

The arrangement illustrated in FIGS. 10 and 11 differs from those described and illustrated hereinbefore in that it is intended for use in the extrusion of hollow members. The die comprises a female part 30 defining a plurality of openings. Each opening receives part of a male part 32. The male and female parts 30, 32 define therebetween die cavities 18. Each die cavity 18 is of zero bearing form and includes leading edges 18a defined by the male and female parts 30, 32. The male part 32 will deflect relative to the female part 30, in use, as described hereinbefore. Such deflection would, in a typical arrangement result in the leading edges 18a, 18b becoming misaligned. In accordance with the invention the die is designed such that, at rest, the leading edges 18a defined by the male part 32 are spaced from those defined by the female part 30 in the extrusion direction and such that, in use, the deflection of the male part 32 results in the spacing of the leading edges 18a, 18b reducing, thus reducing, for example, the tendency of a circular cross-section extrusion to become elliptical. Preferably the spacing of the leading edges 18a, 18b is reduced to zero in the extrusion direction, in use, but reducing the spacing to a very small amount may be acceptable in some circumstances.

In order to manufacture an extrusion die in accordance with the invention it is necessary to determine how much each part of the die will deflect, in use. Once the deflection has been determined, the die can be designed to ensure that, in its deflected, in use condition, the leading edge at one side of the die cavity aligns or substantially aligns with that at the opposite side of the cavity for all parts of the die.

The determination of how much deflection will occur can be achieved using a range of techniques. For example, a skilled technician may be able to determine, from his own knowledge and to a reasonable degree of accuracy, how much deflection is likely. In an alternative technique, a computer model may be used to determine the forces likely to be experienced by parts of a die, and hence the likely deflection of those parts. The model conveniently uses a finite element analysis approach. In another technique, a die having a cavity and other characteristics similar to the die to be manufactured may have a load applied thereto and the deflection of parts thereof measured.

Figure 12:
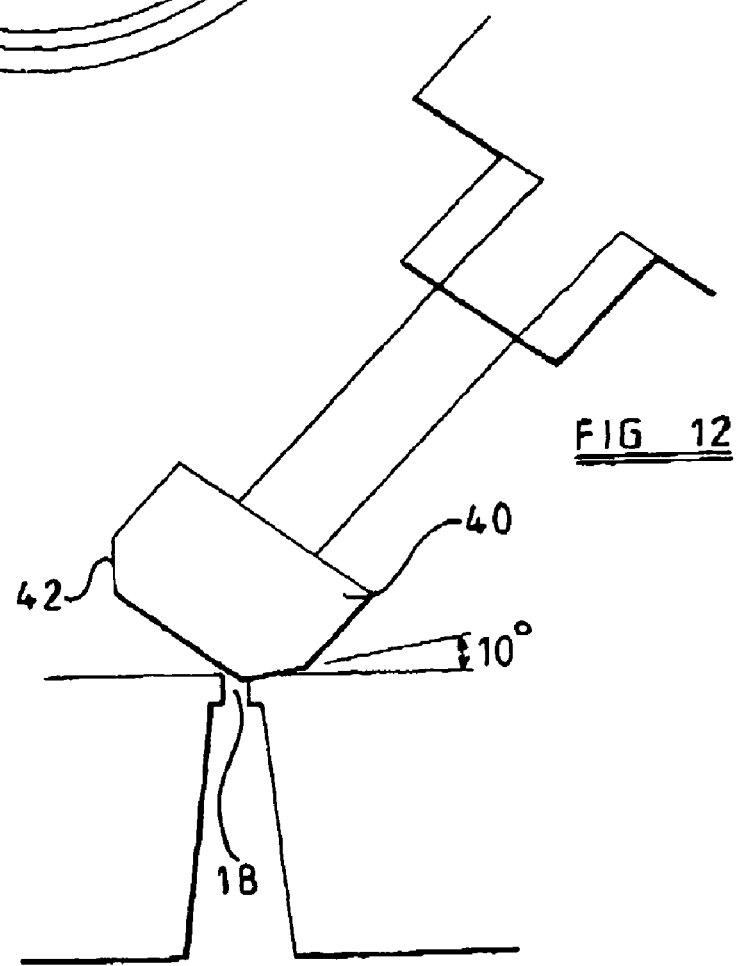
FIG. 12 is a diagrammatic view illustrating part of a method for use in manufacturing the dies of FIGS. 1 to 11.

Once the likely deflection has been determined, recesses are formed around the die cavity, the recesses being shaped, and in particular the depth of the recesses being controlled, to ensure that, in its deflected state, proper alignment of the leading edges occurs. The formation of the recesses is conveniently achieved using a grinding process. FIG. 12 illustrates a grinding wheel 40 having a grinding surface 42 of frusto-conical shape. The grinding wheel 40 is mounted for rotation about an axis angled to the intended extrusion direction to form a recess, the base of which is angled at 10° to the front face of the die. The wheel 40 is conveniently of diameter approximately 15 mm.

In order to improve the wear resistance of the die, a nitriding process is also preferably undertaken.

Although as described above a grinding technique may be used to form the recess, other techniques could be used, if desired.

The invention claimed is:

1. An extrusion die comprising a die body having a die cavity formed therein, the die body defining a male portion which projects into a female portion, a recess of non-uniform depth being provided on the die body ahead of the die cavity in the extrusion direction, the recess being of non-uniform depth both around and across the die cavity, wherein a leading edge of a part of the die cavity defined by the male portion and a leading edge of an opposing part of the die cavity defined by the female portion are out of alignment with one another when the die is not in use, at least part of at least one of the leading edges being defined at the intersection between the die cavity and the recess, wherein the die body has a leading face wherein the die cavity is formed, and wherein the leading face is non-planar whereby the male portion is raised relative to the female portion resulting in the leading edge of the part of the die cavity defined by the male portion being spaced, in the extrusion direction, ahead of the leading edge of the part of the die cavity defined by the female portion by a distance which is not uniform around the die cavity, the spacing being such that deflection of the male portion, in use, brings the leading edges substantially into alignment.

2. A die as claimed in claim 1, wherein the die cavity is of zero bearing form, both the male and the female portions being zero bearing.

3. A die as claimed claim 1, wherein the male and female portions co-operate to produce, in use, an extrusion having at least one channel shaped region.

4. A die as claimed claim 1, wherein the die body has plural parts, the male and female portions being on separate die parts and co-operate to produce, in use, an extrusion including at least one hollow region.

5. A die as claimed claim 1, wherein the extrusion die is a flat face die.

6. A die as claimed in claim 1, wherein the die body is a unitary structure, the male and female portions are on that unitary body.

7. A die as claimed in claim 1, wherein the non-uniform depth across the die cavity results from the male and female portions being of different depths of the recess on the respective male and female portions, and the non-uniform depth around the die cavity results from the depth of at least one of the portions differing itself.

8. An extrusion die comprising a die body having a die cavity formed therein, the die body defining a male portion which projects into a female portion, wherein a leading edge of a part of the die cavity defined by the male portion and a leading edge of an opposing part of the die cavity defined by the female portion are out of alignment with one another when the die is not in use, the leading edge of the part of the die cavity defined by the male portion being spaced by a distance, in the extrusion direction, ahead from the leading edge of the part of the die cavity defined by the female portion, the distance varying around the die cavity, the spacing being such that deflection of the male portion and female portion, in use, brings the opposing leading edges substantially into alignment.

9. A die as claimed in claim 8, wherein the spacing varies smoothly and continuously over the face of the die.

10. A die as claimed in claim 9, wherein the spacing varies smoothly and continuously over the face of the die from a maximum at tips of the male portions to a minimum at ends remote therefrom.

* * * * *